(12) United States Patent
Apgar et al.

(10) Patent No.: US 6,364,881 B1
(45) Date of Patent: Apr. 2, 2002

(54) LONGITUDINALLY ADJUSTABLE BONE PLATES AND METHOD FOR USE THEREOF

(75) Inventors: Mark E. Apgar, Laguna Niguel; Kyle Hayes, Mission Viejo, both of CA (US)

(73) Assignee: Interpore Cross International, Irvine, CA (US)

( * ) Notice: Subject to any disclaimer, the term of this patent is extended or adjusted under 35 U.S.C. 154(b) by 0 days.

(21) Appl. No.: 09/426,356

(22) Filed: Oct. 25, 1999

Related U.S. Application Data

(63) Continuation-in-part of application No. 08/902,710, filed on Jul. 30, 1997, now Pat. No. 5,984,925.

(51) Int. Cl.[7] ............................................. A61B 17/80
(52) U.S. Cl. ......................................... 606/69; 606/60
(58) Field of Search ............................. 606/60, 61, 69, 606/70, 71–73

(56) References Cited

U.S. PATENT DOCUMENTS

| | | | | |
|---|---|---|---|---|
| 1,105,105 A | * | 7/1914 | Sherman | 606/69 |
| 3,534,731 A | * | 10/1970 | Muller | 606/105 |
| 3,716,050 A | * | 2/1973 | Johnston | 606/69 |
| 4,219,015 A | * | 8/1980 | Steinemann | 606/69 |
| 4,493,317 A | * | 1/1985 | Klaue | 606/69 |
| 4,573,458 A | * | 3/1986 | Lower | 606/69 |
| 4,771,767 A | * | 9/1988 | Steffee | 606/61 |
| 4,905,679 A | * | 3/1990 | Morgan | 606/70 |
| 5,139,497 A | * | 8/1992 | Tilghman et al. | 606/69 |
| 5,190,544 A | * | 3/1993 | Chapman et al. | 606/69 |
| 5,209,751 A | * | 5/1993 | Farris et al. | 606/61 |
| 5,336,224 A | * | 8/1994 | Selman | 606/69 |
| 5,372,598 A | * | 12/1994 | Luhr et al. | 606/69 |
| 5,413,577 A | * | 5/1995 | Pollock | 606/69 |
| 5,415,661 A | * | 5/1995 | Holmes | 606/669 |
| 5,423,826 A | * | 6/1995 | Coates et al. | 606/96 |
| 5,468,242 A | * | 11/1995 | Reisberg | 606/69 |
| 5,569,250 A | * | 10/1996 | Sarver et al. | 606/69 |
| 5,578,036 A | * | 11/1996 | Stone et al. | 606/69 |
| 5,591,169 A | * | 1/1997 | Benoist | 606/69 |
| 5,690,631 A | * | 11/1997 | Duncan et al. | 606/69 |
| 5,709,686 A | * | 1/1998 | Talos et al. | 606/69 |
| 5,746,742 A | * | 5/1998 | Runciman et al. | 606/69 |
| 5,752,958 A | * | 5/1998 | Wellisz | 606/69 |
| 5,785,712 A | * | 7/1998 | Runciman et al. | 606/69 |
| 5,902,304 A | * | 5/1999 | Walker et al. | 606/71 |
| 5,951,557 A | * | 9/1999 | Luter | 606/69 |
| 5,984,925 A | * | 11/1999 | Apgar | 606/69 |

* cited by examiner

Primary Examiner—Gene Mancene
Assistant Examiner—Michael B. Priddy
(74) Attorney, Agent, or Firm—Hudak & Shunk Co. L.P.A.

(57) ABSTRACT

The invention relates to a bone plate having at least two and up to ten ringed eyelets for receiving anchoring bone screws in a modified ball-and-socket joint. The eyelets are longitudinally aligned and joined to neighboring eyelets by curvilinear, bendable ribs extending between pairs of eyelets. The ribs are of a longer length than the distance between the external surfaces of adjacent rings which allows the longitudinal spacing of the rings to be increased or decreased by bending the ribs.

7 Claims, 5 Drawing Sheets

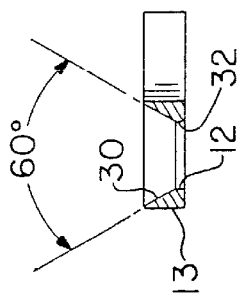
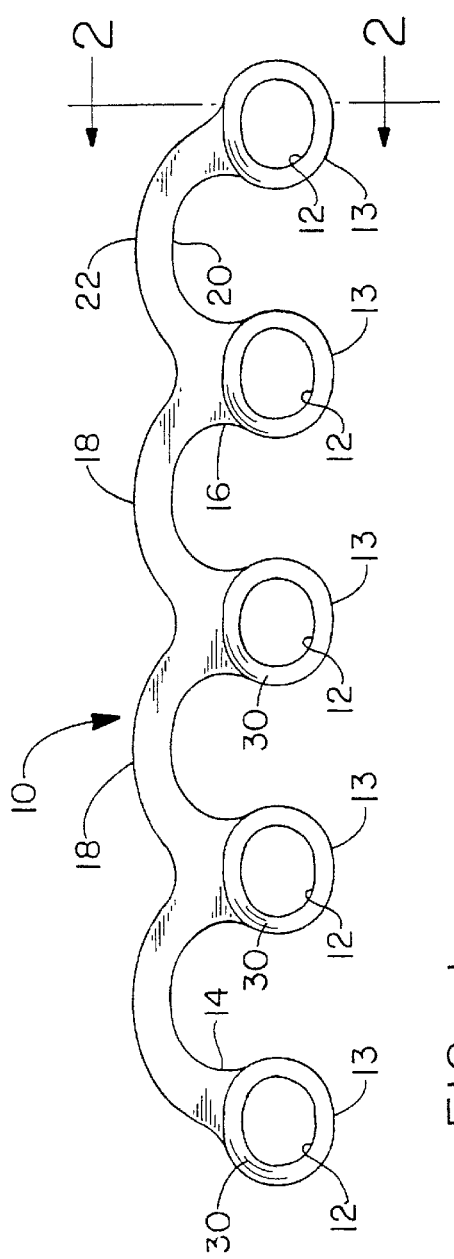
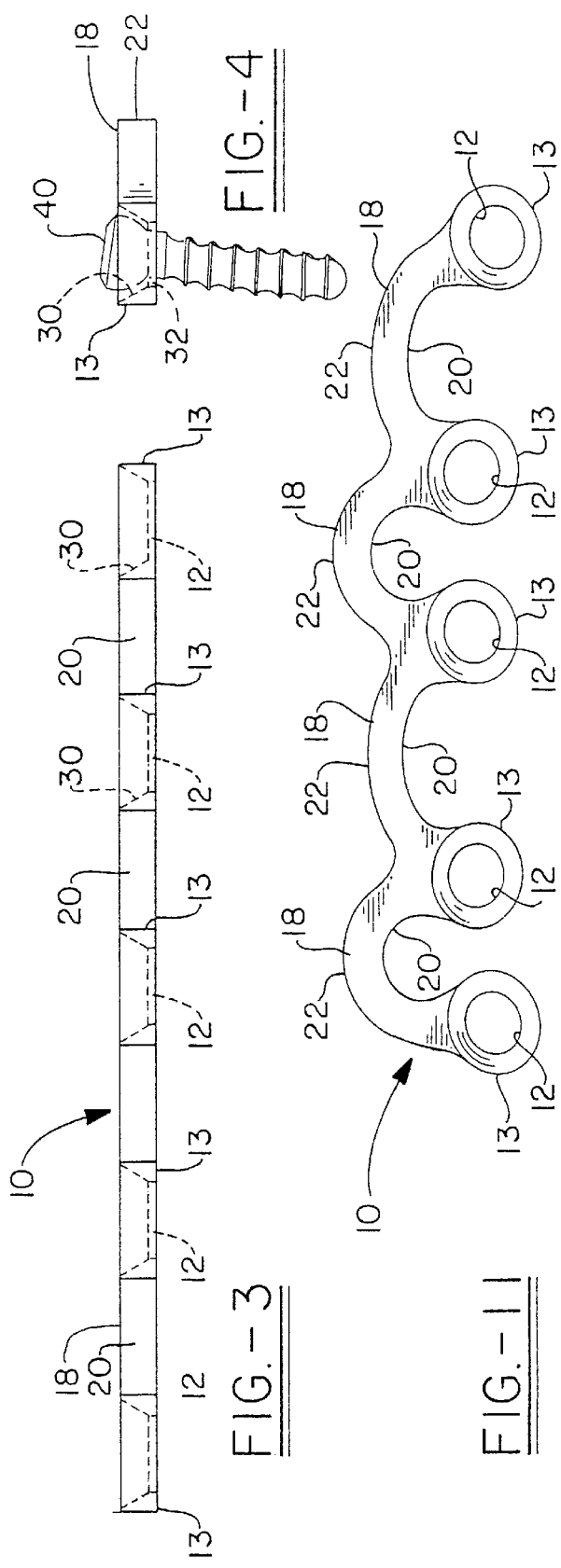

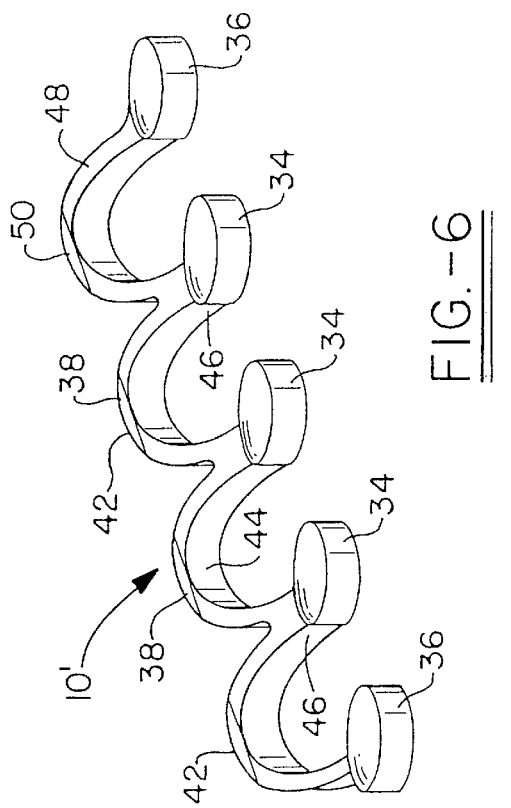
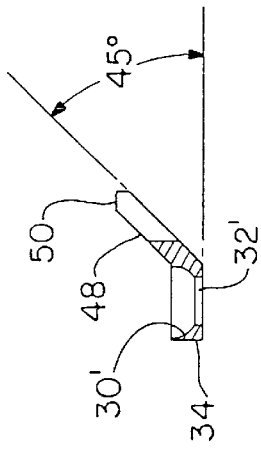
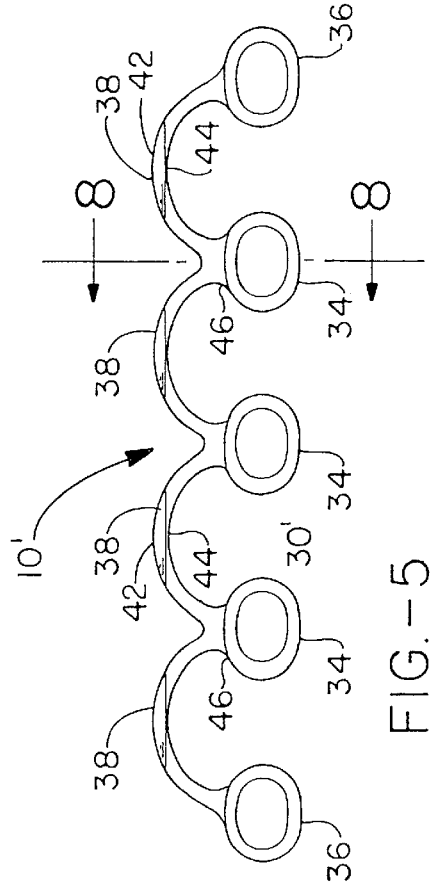
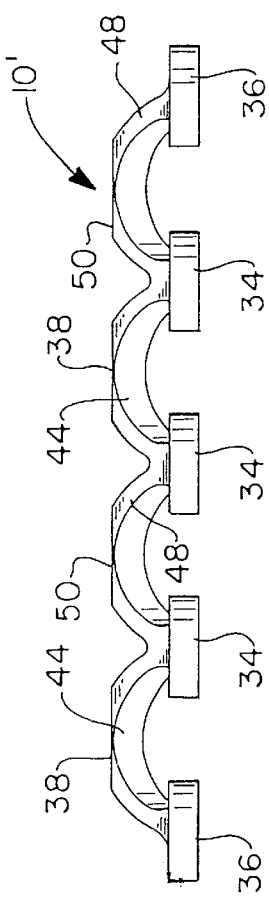
FIG.-5
FIG.-6
FIG.-7
FIG.-8

LONGITUDINALLY ADJUSTABLE BONE PLATES AND METHOD FOR USE THEREOF

CROSS REFERENCE

This is a Continuation-In-Part Application of U.S. Ser. No. 08/902,710, filed Jul. 30, 1997 now U.S. Pat. No. 5,984,925 for LONGITUDINALLY ADJUSTABLE BONE PLATES AND METHOD FOR USE THEREOF.

FIELD OF INVENTION

The invention relates generally to a plate used for bone stabilization and more particularly to plates having means to adjust the spacing between points of attachment to the bone or bones along the longitudinal axis. In a further embodiment the adjustment means is designed to accordion in a way which maintains the longitudinal alignment of the points of attachment.

BACKGROUND OF THE INVENTION

Orthopaedic implants have long been used for the stabilization of bones. For example, plates have been used in conjunction with screws on long bones, and screws and hooks have been used in conjunction with rod seats and rods in the spine as a method of treating traumatic injuries as well as to correct severe misalignments such as scoliosis.

While plates have the advantage of simplifying assembly during surgical implantation, traditional applications of plates have not been as flexible as other means of fixation such as rods and anchors due to the fact that plates do not allow for longitudinal variation of the spacings at the fixation site. For some sites or bone conditions, the exact location for fixation may be limited and in such instances it is extremely advantageous to be able to readily adapt to the site by reshaping a plate and also to be able to vary the angle of entry of the anchoring screw(s) or other anchoring means.

It is therefore an object of the present invention to provide a fixation or stabilization plate for surgical implantation in humans or other animals wherein the location of the anchoring sites along the longitudinal axis can be varied by increasing or decreasing the distance.

It is a further object of the invention to provide a bone plate in which the alignment of the fixation sites along the longitudinal site can be varied.

It is a further object of the invention to provide a plate having fixation sites which enable variation in the angle of entry of an anchor such as a bone screw.

It is a further object of the invention to provide a plate having variable screw spacing substantially along a single axis.

BRIEF DESCRIPTION OF DRAWINGS

FIG. 1 is a top plan view of a first embodiment of a bone plate in accordance with the invention;

FIG. 2 is a cross-sectional view taken along lines 2—2;

FIG. 3 is a side view of the plate of FIG. 1;

FIG. 4 is an end view of the plate in accordance with FIG. 1;

FIG. 5 is a top view of a second embodiment of the invention;

FIG. 6 is a perspective view of the plate in accordance with the invention;

FIG. 7 is a side view of the plate of FIG. 5;

FIG. 8 is a cross-sectional view of the second embodiment of the invention taken along lines 8—8 of FIG. 5;

FIG. 11 is a top view of the first embodiment of the invention which has been bent to accommodate a different spacing;

DETAILED DESCRIPTION OF INVENTION

Figure 9:
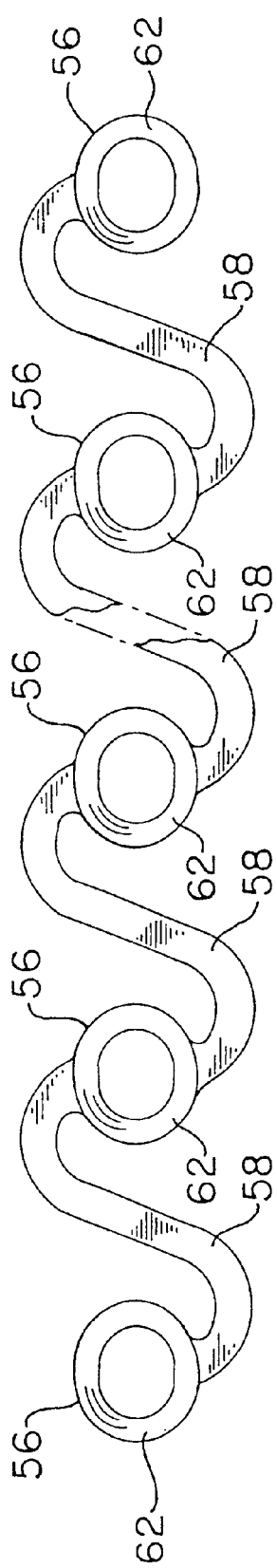
FIG. 9 is a top view of a third embodiment of the invention.

A plate in accordance with the invention is illustrated generally at 10 in FIG. 1. An unaltered plate (i.e., prior to site-specific bending) includes a series of anchoring sites or holes, i.e., eyelets 13 (or rimmed holes for receiving bone screws), which are longitudinally aligned and which are intended to receive an anchoring element such as, for example, a bone screw, in order to anchor the plate 10 to an appropriate bone or bones. Of course, other anchoring means could be used such as a pin, rivet, wedge, and/or cement or the like. The eyelets are connected by a sinuous, bendable structure or rib characterized in that it does not include a linear portion which is longitudinally aligned with the long axis of the plate and, in fact, includes repeating "C" shapes or "S" shapes so that no linear longitudinally aligned structure exists. As used herein, longitudinal axis refers to an imaginary axis at the center of the plate which extends in the long direction of the plate; the actual connecting portion of the plate may be offset. The ribs may include a linear portion which diagonally transverses the long axis or may arch between eyelets leaving a space or void along the longitudinal axis between eyelets. Thus, it can be seen that the rib is longer than the longitudinal distance between eyelets which enables this distance to be varied by bending the ribs. The plate can be used on the spine, for example, on the sacrum, or on larger bones such as the pelvis, or on long bones.

In a further embodiment of the invention a bone plate is provided which has members linking the eyelets having a structure such that eyelets tend to retain longitudinal alignment during compression or expansion of the distance. In particular, this is achieved by forming an arch preferably having a width at the apex which is less than its thickness. The resulting plate has a tendency to accordion in length while retaining the longitudinal alignment of the eyelets. Thus, the arch will bend rather than buckle in or out of the plane of the eyelets. The necked areas of adjoining links is also cut out in order to permit a tool to be used to bend or expand the plate and thereby change the relative position of the bony segments joined to the eyelets.

In a further embodiment of the invention the arched ribs or link member 118, which bridges the eyelets 113 is shaped to encourage a particular bending behavior. Specifically, the link has an arch shape with an apex that is more severely curved on the interior minor curve and, in fact, mimics a V-shaped return 120 on the inside with a U-shaped return on the exterior surface 122. Further, this arch has supporting columnar side shapes 119 which widens in the lateral dimension from the apex 123 to the area joining the eyelets.

The lateral dimension or "width" Z is less than the "thickness" Y. In particular, the width is at least 10%, preferably at least 15% less than the thickness and down to 45% or 50% less than this value. More preferably, the width is 15–25% or around 20% of the dimension of the cross-sectional thickness. However, while the linking member has a shape which controls the bending so as to maintain the alignment of the eyelets, it still maintains a smoothly flowing, organic shape to avoid sharp edges or areas which will concentrate stress so as to provide areas vulnerable to cracking or breaking during bending.

In practice, two plates may be used in tandem, for example, one on either side of the area of fixation. The force necessary to bend the individual linking member between eyelets of a single plate is at least 20 pounds, and preferably at least 25 pounds or more. Together is envisioned that two plates will resist at least 40 pounds of force tending to push against the plates.

An additional aspect of the invention provides a cut-out 124 into the necked area 116 of linking members. Specifically, the intermediate eyelets each have two linking members which join together to form a necked area 116 that is substantially transverse to the longitudinal axis as defined by the eyelets 113. The necked area can include a U-shaped or slot-shaped cut out which will accept the prongs or pins of an instrument to bend the linking member in situ.

Each eyelet 13 includes a recessed portion 30 which forms an angle of about 30° on either side of a ling perpendicular to the longitudinal axis, for a total angle of 60° as illustrated in FIG. 2. The recessed portion 30 terminates in an oval shape through bore 12. The eyelet has a 60° angle on its internal slope. The slot is from about 4 to about 5 mils, and preferably about 5.3 mils long, and from about 4 to about 5 mils, and preferably about 4.3 mils wide. The bore 12 includes a necked portion 32, which secures the rounded bottom portion of a head of an anchoring screw 40 as illustrated in phantom in FIG. 4. This cooperation forms a limited ball and socket joint. The ovoid or elongated shape, along with the narrower necked portion, allows the screw 40 to be implanted at various angles of insertion to best access the anchoring site.

The eyelets 13 are connected by a series of arched ribs 18 having a smooth external radius 22 and internal radius 20 joining together at adjacent eyelets to provide a necked portion 16. The ribbed portion can be bent to enable the distance between neighboring eyelets to be varied and more particularly, to enable a shorter or longer distance between the eyelets and specifically between the points of fixation. A preferred standard distance (for an unaltered plate) is 16 millimeters between the center of each eyelet; however, manipulation of the plate can allow an increase of up to 18 to 20 millimeters or, conversely, the distance can be collapsed down to 10 millimeters (i.e., a distance of around 9 millimeters between the central longitudinal axes of the screws). Manipulation of the plate allows elongation or an increase in the distance between slots of about 2 to about 4 mils or, alternatively, the slots can be compressed until the external diameters are touching.

Preferably, the ribs 18 have a smooth radius for better stress distribution and better biocompatibility.

The plate is from about 1.5 to 4 mils, preferably about 2 to 3.5 mils, and most preferably about 2.5 mils in thickness to resist axial loading. It is preferred that the plate will be made of a suitable surgical material such as surgical-grade stainless steel or titanium and will deform (i.e., can be longitudinally compressed or expanded) in excess of 40 Newtons of force using a spreader compressor.

The curve 20 used on the inside radius of the rib has a radius of from about 5.5 to about 7 mils. The outside radius is from about 8 to about 10 mils, each radius being ±2 mils and preferably ±1 mil, that is, about 6 to about 7 mils on the inside, and about 8.5 to about 9.5 mils on the outside.

The plate may include as few as one linkage, i.e., one rib and two eyelets, or may include as many as nine linkages, but preferably includes four to seven linkages, i.e., five eyelets and four ribs, six eyelets and five ribs, or seven eyelets and six ribs.

A second embodiment of the invention is shown in FIGS. 5–8. Again, the plate 30 comprises a series of eyelets 33 connected by a series of arched ribs 38 having a smooth external radius 42 and internal radius 40. Again the ribs 38 joining the intermediate eyelets 34, i.e. excluding the first and last eyelet 36, come together to form a necked area 46. The ribs are configured substantially as described above and again include elongated slots 12 having sloped sides to permit variable angulation of the anchoring screw or other anchoring means.

The plates in embodiments 1 and 2 may be used in tandem to provide symmetry in use. For example, two plates may be used together with opposing eyelets or alternatively opposing ribs.

Figure 10:
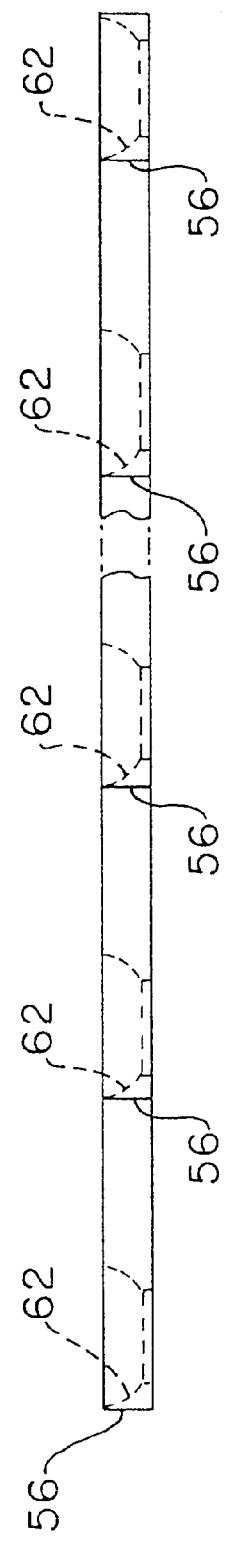
FIG. 10 is a side view of the embodiment shown in FIG. 9 illustrating the anchor holes in phantom.
Figure 12:
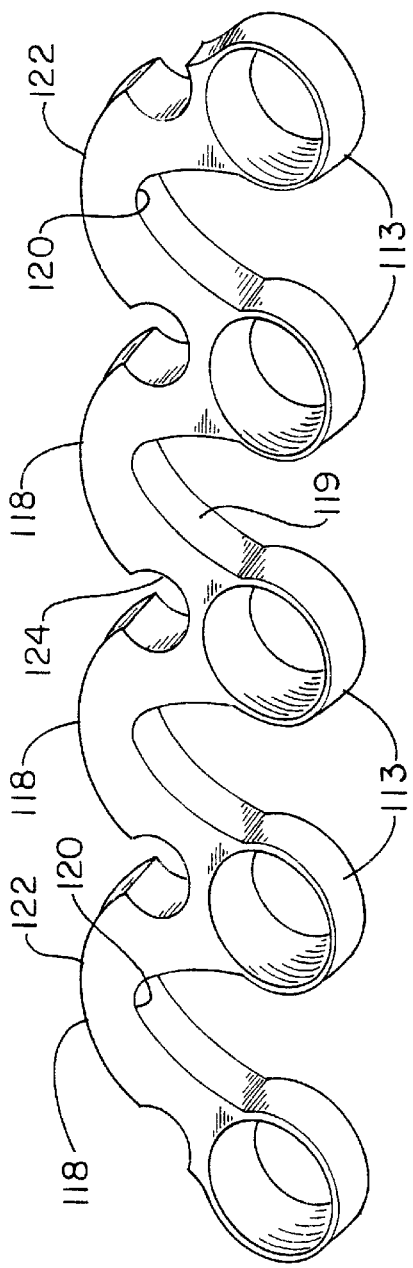
FIG. 12 is a top perspective view of a further embodiment of the invention.
Figure 13:
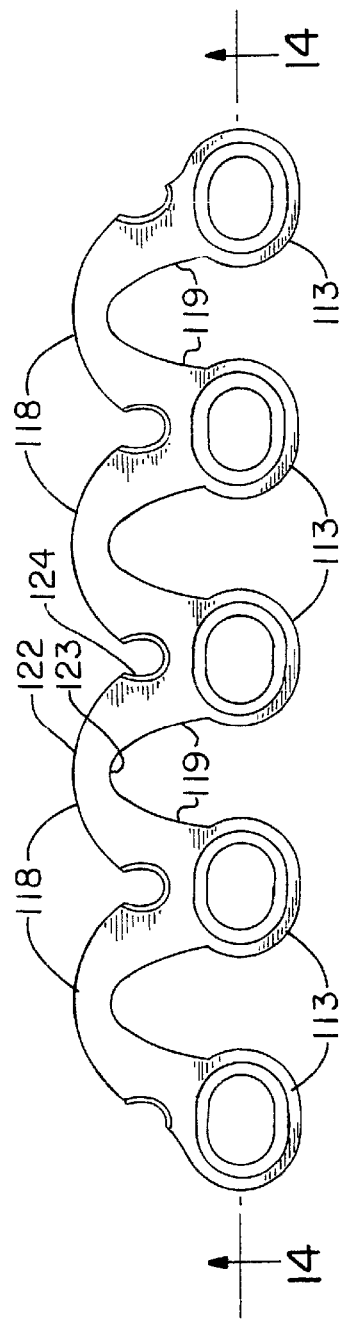
FIG. 13 is a top plan view of the embodiment shown in FIG. 12.
Figure 14:
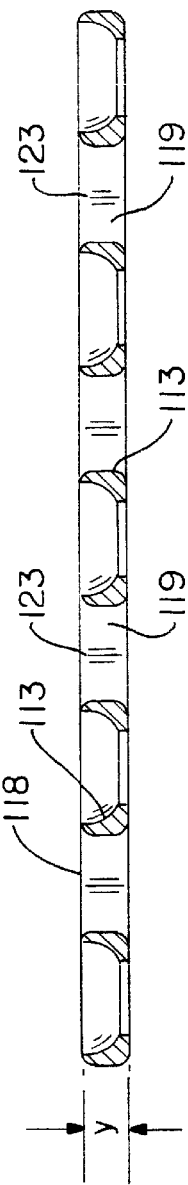
FIG. 14 is a cross-section taken along line 13—13 of FIG. 13.
Figure 15:
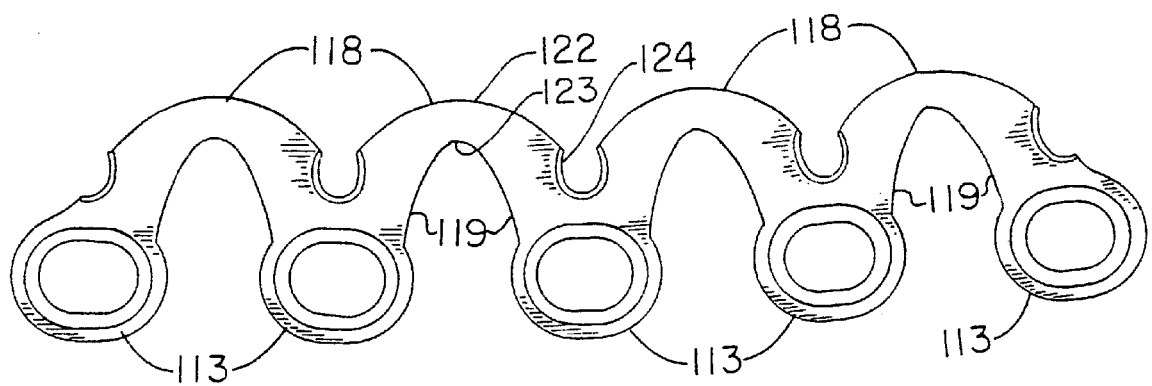
FIG. 15 is a top view of the embodiment of FIG. 12 which has been bent to accommodate a different spacing.

FIGS. 9 and 10 represent a third laterally symmetrical embodiment having similar eyelets 36 with elongated slots 62. The eyelets 56 are connected by ribs 58 having inward and outward curves (i.e., forming a gentle "S" shape transversing the longitudinal axis and curing beyond the outer rim of the eyelets on either side). This embodiment is planar. The location of the eyelets can be changed by bending the ribs to alter the relative spacing. This embodiment includes a lateral rise 48 in the curved rib portion to allow for variations in bone topography. The rib may include an angle, as illustrated in FIG. 8, of from about 15° to about 60°, and preferably about 45°±10°. It is preferred that the overall height be restricted to about 7 to about 8 mils, and that the top portion of the rib include a flat 50 in order to avoid a sharp edge on the top.

A third embodiment is shown in FIGS. 9 and 10 and also includes eyelets 56 having elongated anchor slots 62 for fixation to the bone and curved S- shaped ribs 58 which connect the eyelets 56 and extend both below and above the longitudinal axis. The embodiment may expand from about 16 to about 21 mils and collapse to about 9 mils.

FIG. 11 illustrates how a plate (as shown in FIG. 1) can be bent in order to accommodate an irregular spacing.

While in accordance with the patent statutes the best mode and preferred embodiment has been set forth, the scope of the invention is not limited thereto, but rather by the scope of the attached claims.

What is claimed is:

1. A rigid bone plate having at least two eyelets joined by a curved link member, wherein said link member tapers to a narrowest portion having a width Z which is less than its thickness Y.

2. A rigid bone plate as set forth in claim 1, wherein said link member defines an arch.

3. A rigid bone plate as set forth in claim 1, wherein said width Z is at least 10% less than said thickness Y.

4. A rigid bone plate as set forth in claim 3, wherein said width Z is at least 15% less than said thickness Y.

5. A rigid bone plate as set forth in claim 4, wherein said width Z is at least 20% less than said thickness Y.

6. A rigid bone plate as set forth in claim 1, wherein said link member has an inside minor surface member which defines V-shape.

7. A rigid bone plate comprising:
at least 4 eyelets substantially aligned in a single axis and each joined to a successive, continguous eyelet by a link member, said plate having;
a first terminal eyelet and a second terminal eyelet and intermediate eyelets there between, said intermediate eyelets having a necked area formed by adjacent link members; and
said necked area including a cut-out capable of accommodating instrumentation used for bending link members.

* * * * *